United States Patent [19]

Elbe et al.

[11] Patent Number: 4,500,537

[45] Date of Patent: Feb. 19, 1985

[54] COMBATING FUNGI WITH TRIAZOLYL-VINYL KETONES AND CARBINOLS

[75] Inventors: Hans-Ludwig Elbe, Wuppertal; Karl H. Büchel, Burscheid; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 494,216

[22] Filed: May 13, 1983

Related U.S. Application Data

[63] Continuation of Ser. No. 259,303, Apr. 30, 1981, abandoned.

[30] Foreign Application Priority Data

May 19, 1980 [DE] Fed. Rep. of Germany ....... 3019046

[51] Int. Cl.³ .................... A01N 43/64; A01N 55/02; C07D 249/08; C07F 1/08
[52] U.S. Cl. .................................. 514/383; 548/101; 548/262; 514/184
[58] Field of Search ............... 548/101, 262; 542/428, 542/468, 400; 424/245, 269

[56] References Cited

U.S. PATENT DOCUMENTS 4,086,351 4/1978 Balasubramanyan et al. ..... 542/429
4,182,862 1/1980 Chan ................... 548/262
4,203,995 5/1980 Funaki et al. .................. 424/269

Primary Examiner—Alton D. Rollins
Attorney, Agent, or Firm—Sprung Horn Kramer & Woods

[57] ABSTRACT

A triazolyl-vinyl ketone or carbinol of the formula

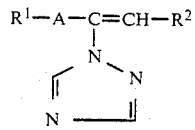

in which
 A represents the keto group or a CH(OH) grouping,
 $R^1$ represents alkyl or halogenoalkyl and
 $R^2$ represents a primary or tertiary alkyl radical, halogenoalkyl, alkoxyalkyl, alkylmercaptoalkyl, dialkylaminoalkyl, hydroxyalkyl, an optionally substituted alkenyl, alkynyl or alkenynyl radical, phenylalkyl which is optionally substituted in the alkyl part and/or in the phenyl part, an optionally substituted indenyl or fluorenyl radical, or an optionally substituted diphenylmethyl or triphenylmethyl radical, or an addition product thereof with a physiologically acceptable acid or a metal salt, which possesses fungicidal activity.

9 Claims, No Drawings

COMBATING FUNGI WITH TRIAZOLYL-VINYL KETONES AND CARBINOLS

This is a continuation of application Ser. No. 259,303, filed Apr. 30, 1981, abandoned.

The present invention relates to certain new triazolyl-vinyl ketones and carbinols, to a process for their preparation and to their use as fungicides.

It has already been disclosed that certain 1-phenyl-2-triazolyl-4,4-dimethyl-1-penten-3-ones and -ols have a good fungicidal activity (see, for example, DE-OS (German Published Specification) 2,838,847). However, the action of these compounds is not always completely satisfactory, especially when low amounts and concentrations are applied.

The present invention now provides, as new compounds, the triazolyl-vinyl ketones and -carbinols of the general formula

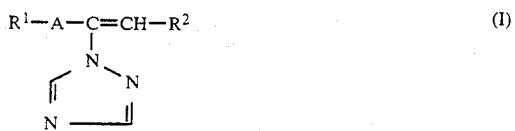

in which
A represents the keto group or a CH(OH) grouping,
$R^1$ represents alkyl or halogenoalkyl and
$R^2$ represents a primary or tertiary alkyl radical, halogenoalkyl, alkoxyalkyl, alkylmercaptoalkyl, dialkylaminoalkyl, hydroxyalkyl, optionally substituted alkenyl, alkynyl or alkenynyl, phenylalkyl which is optionally substituted in the alkyl part and/or in the phenyl part, an optionally substituted indenyl or fluorenyl radical, or an optionally substituted diphenylmethyl or triphenylmethyl radical,
and physiologically acceptable acid addition salts and metal salt complexes thereof.

The compounds of the general formula (I) can exist in two geometric isomer forms (E-form and Z-form), depending on the arrangement of the groups bonded to the double bond; they are preferentially obtained in a varying E/Z-isomer ratio. If A represents the CH(OH) grouping, an asymmetric carbon atom is present, so that in this case the compounds of the formula (I) are also obtained in two optical isomer forms; they are preferentially obtained as racemates. The formula (I) embraces not only the individual isomers but also the isomer mixtures.

The invention also provides a process for the preparation of a triazolylvinyl ketone or -carbinol of the formula (I), in which a keto-enamine of the general formula

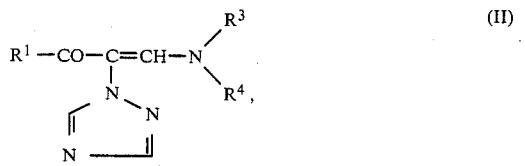

in which
$R^1$ has the abovementioned meaning and
$R^3$ and $R^4$ are identical or different and represent alkyl, is reacted with an organo-magnesium compound of the general formula

in which
$R^2$ has the abovementioned meaning and
Hal represents halogen, in the presence of a solvent, and, if appropriate, the keto derivative formed, of the formula (I), is reduced. The reduction can be effected in the customary manner.

An acid or a metal salt can optionally be subsequently added onto the compound of the formula (I) thus obtained.

The triazolyl-vinyl ketones and -carbinols of the formula (I) have powerful fungicidal properties. Surprisingly, the compounds according to the invention exhibit a better fungicidal activity than the 1-phenyl-2-triazolyl-4,4-dimethyl-1-penten-3-ones and -ols which are known from the state of the art and are closely related compounds chemically and from the point of view of their action. The substances according to the invention thus represent an enrichment of the art.

The formula (I) provides a general definition of the triazolyl-vinyl ketones and -carbinols according to the invention. Preferably, in this formula,
$R^1$ represents straight-chain or branched alkyl with 1 to 6 carbon atoms or straight-chain or branched halogenoalkyl with 1 to 4 carbon atoms and 1 to 5 identical or different halogen atoms (especially fluorine, chlorine and bromine atoms),
$R^2$ represents straight-chain or branched primary or tertiary alkyl with 1 to 29 carbon atoms (especially 1 to 18); straight-chain or branched halogenoalkyl with 1 to 29 (especially 1 to 18) carbon atoms and 1 to 5 identical or different halogen atoms (especially fluorine, chlorine and bromine atoms); alkoxyalkyl or alkoxymercaptoalkyl with in either case 1 to 4 carbon atoms in each alkyl part; straight-chain or branched dialkylaminoalkyl with 1 to 4 carbon atoms in each alkyl radical of the amino group and 1 to 29 (especially 1 to 18) carbon atoms in the alkyl part; straight-chain or branched hydroxyalkyl with 1 to 29 (especially 1 to 18) carbon atoms; an optionally substituted straight-chain or branched alkenyl, alkynyl or alkenynyl radical with in each case up to 6 carbon atoms, the or each substituent being selected from hydroxyl, cyano, nitro, alkoxy with 1 to 4 carbon atoms and phenyl, which can optionally carry one or more substituents selected independently from halogen (especially fluorine and chlorine), alkyl with 1 to 4 carbon atoms, alkoxy and alkylthio with in either case 1 to 4 carbon atoms and halogenoalkoxy and halogenoalkylthio with in either case 1 to 4 carbon atoms and 1 to 5 identical or different halogen atoms (such as, in particular, fluorine and chlorine atoms); phenylalkyl which has 1 to 4 carbon atoms in the alkyl part (especially benzyl) and which can optionally carry one or more substituents on the phenyl selected independently from halogen (especially fluorine and chlorine), alkyl with 1 to 4 carbon atoms, alkoxy and alkylthio with in either case 1 to 4 carbon atoms and halogenoalkoxy and halogenoalkylthio with in either case 1 to 4 carbon atoms and 1 to 5 identical or different halogen atoms (such as, in particular, fluorine and chlorine atoms), and which can optionally carry one or more substituents on the alkyl selected independently from cyano, hydroxycarbonyl and alkoxycarbonyl with 1 to 4 carbon atoms in the alkyl part; an indenyl or fluorenyl radical which is optionally substituted by halogen or alkyl or alkoxy with in each case 1 to 4 carbon atoms; or a diphenylmethyl or triphenylmethyl radical, optionally carrying one or more substituents on the phenyl selected independently from halogen (especially fluorine and chlorine), alkyl with 1 to 4 carbon atoms, alkoxy and alkylthio with in either case 1 to 4 carbon atoms and halogenoalkoxy and halogenoalkylthio with in either case 1 to 4 carbon atoms and 1 to 5 identical or different halogen atoms (such as, in particular, fluorine and chlorine atoms).

Particularly preferred compounds of the formula (I) are those in which $R^1$ represents tert.-butyl, chloro-tert.-butyl, fluoro-tert.-butyl, dichloro-tert.-butyl or difluoro-tert.-butyl.

The following compounds of the general formula (I) may be mentioned specifically, in addition to the compounds mentioned later in the preparative examples:

TABLE 1

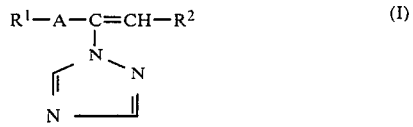

| $R^1$ | $R^2$ | A |
|---|---|---|
| Cl—CH$_2$—C(CH$_3$)$_2$— | —CH$_2$—⌬ | CO |
| Cl—CH$_2$—C(CH$_3$)$_2$— | —C≡C—⌬ | CO |
| Cl—CH$_2$—C(CH$_3$)$_2$— | —C(CH$_3$)$_3$ | CO |
| F—CH$_2$—C(CH$_3$)$_2$— | —CH$_2$—⌬ | CO |
| F—CH$_2$—C(CH$_3$)$_2$— | —C≡C—⌬ | CO |
| F—CH$_2$—C(CH$_3$)$_2$— | —C(CH$_3$)$_3$ | CO |
| CH$_3$—C(CH$_2$Cl)$_2$— | —CH$_3$ | CO |
| CH$_3$—C(CH$_2$Cl)$_2$— | —C$_2$H$_5$ | CO |
| CH$_3$—C(CH$_2$Cl)$_2$— | —C(CH$_3$)$_3$ | CO |
| CH$_3$—C(CH$_2$Cl)$_2$— | —C$_6$H$_{13}$—n | CO |
| CH$_3$—C(CH$_2$Cl)$_2$— | —CH$_2$—⌬ | CO |
| CH$_3$—C(CH$_2$Cl)$_2$— | —C≡C—⌬ | CO |
| CH$_3$—C(CH$_2$F)$_2$— | —CH$_3$ | CO |
| CH$_3$—C(CH$_2$F)$_2$— | —C$_2$H$_5$ | CO |
| CH$_3$—C(CH$_2$F)$_2$— | —C(CH$_3$)$_3$ | CO |
| CH$_3$—C(CH$_2$F)$_2$— | —C$_6$H$_{13}$—n | CO |
| CH$_3$—C(CH$_2$F)$_2$— | —CH$_2$—⌬ | CO |
| CH$_3$—C(CH$_2$F)$_2$— | —C≡C—⌬ | CO |
| (CH$_3$)$_3$C— | —CH$_2$—⌬—OCF$_3$ | CO |

TABLE 1-continued

| $R^1$ | $R^2$ | A |
|---|---|---|
| (CH$_3$)$_3$C— | —CH$_2$—⌬—OCF$_2$CHFCl | CO |
| (CH$_3$)$_3$C— | —CH$_2$—CH$_2$—O—C$_3$H$_7$—n | CO |
| (CH$_3$)$_3$C— | —C$_{23}$H$_{47}$—n | CO |
| (CH$_3$)$_3$C— | —CH$_2$—CH$_2$—S—C$_3$H$_7$—n | CO |
| (CH$_3$)$_3$C— | —(CH$_3$)$_3$—N(CH$_3$)$_2$ | CO |
| (CH$_3$)$_3$C— | —(CH$_2$)$_7$—OH | CO |
| (CH$_3$)$_3$C— | —C(CH$_3$)=CH$_2$ | CO |
| (CH$_3$)$_3$C— | —C(CH$_3$)=CH$_2$ | CO |
| (CH$_3$)$_3$C— | —(CH$_2$)$_7$F | CO |
| (CH$_3$)$_3$C— | —(CH$_2$)$_7$Cl | Co |
| (CH$_3$)$_3$C— | —CH$_2$—⌬—OCF$_3$ | CH(OH) |
| (CH$_3$)$_3$C— | —CH$_2$—⌬—OCF$_2$CHFCl | CH(OH) |
| (CH$_3$)$_3$C— | —CH$_2$—CH$_2$—O—C$_3$H$_7$—n | CH(OH) |
| (CH$_3$)$_3$C— | C$_{23}$H$_{47}$—n | CH(OH) |
| (CH$_3$)$_3$C— | —CH$_2$—CH$_2$—S—C$_3$H$_7$—n | CH(OH) |
| (CH$_3$)$_3$C— | —(CH$_2$)$_3$—N(CH$_3$)$_2$ | CH(OH) |
| (CH$_3$)$_3$C— | —(CH$_2$)$_7$—OH | CH(OH) |
| (CH$_3$)$_3$C— | —C(CH$_3$)=CH$_2$ | CH(OH) |
| (CH$_3$)$_3$C— | —C(CH$_3$)=C(CH$_3$)$_2$ | CH(OH) |
| (CH$_3$)$_3$C— | —(CH$_2$)$_7$F | CH(OH) |
| (CH$_3$)$_3$C— | —(CH$_2$)$_7$Cl | CH(OH) |
| (CH$_3$)$_3$C— | —CH(CN)—⌬—Cl | CH(OH) |
| (CH$_3$)$_3$C— | —C$_6$H$_{13}$—n | CH(OH) |
| (CH$_3$)$_3$C— | —C$_9$H$_{19}$—n | CH(OH) |
| (CH$_3$)$_3$C— | —C$_{12}$H$_{25}$—n | CH(OH) |

If, for example, 4,4-dimethyl-1-dimethylamino-2-(1,2,4-triazol-1-yl)-1-penten-3-one and tert.-butylmagnesium bromide are used as staring materials, the course of the reaction in the process according to the invention can be represented by the following equation:

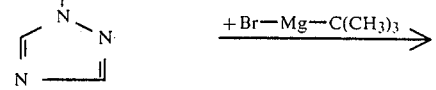

-continued

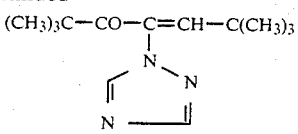

If, for example, 2,2,6,6-tetramethyl-4-(1,2,4-triazol-1-yl)-3-hepten-5-one and sodium borohydride are used as starting materials, the course of the reaction in the reduction according to the invention can be represented by the following equation:

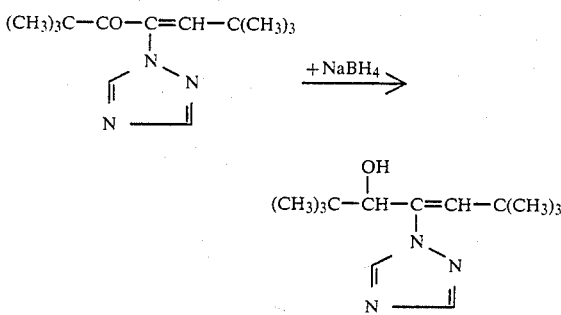

The formula (II) provides a general definition of the keto-enamines to be used as starting materials for the process according to the invention. In this formula $R^1$ preferably represents those radicals which have already been mentioned as preferred for this substituent in connection with the description of the substances of the formula (I). $R^3$ and $R^4$ are identical or different and preferably represent alkyl with 1 to 4 carbon atoms, especially methyl.

The keto-enamines of the formula (II) are the subject of U.S. application Ser. No. 219,154, filed Dec. 22, 1980, now U.S. Pat. No. 4,380,628. The keto-enamines of the formula (II) can be obtained by the processes described in that application, by reacting triazolyl-ketones of the general formula

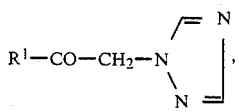

in which $R^1$ has the abovementioned meaning, with amide acetals or aminal esters of the general formula

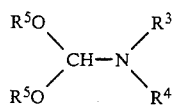

or

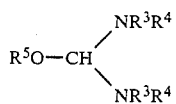

in which
$R^3$ and $R^4$ have the abovementioned meaning and
$R^5$ represents alkyl with 1 to 4 carbon atoms,
in a manner which is in itself known, in the presence of an inert organic solvent, for example an aromatic hydrocarbon, and, especially, an excess of amide acetal or aminal ester of the formula (Va) or (Vb) used, at the boiling point (in this context see also Chem.Ber. 101, 41–50 (1968); J.Org. Chem. 43, 4248–50 (1978) and the preparative examples).

The triazolyl-ketones of the formula (IV) are known (see, for example, DE-OS (German Published Specification) 2,431,407, DE-OS (German Published Specification) 2,610,022 and DE-OS (German Published Specification) 2,638,470), and they can be prepared by customary methods, by reacting the corresponding halogenoketones with 1,2,4-triazole in the presence of an acid-binding agent.

The amide acetals and aminal esters of the formulae (Va) and (Vb) are generally known compounds of organic chemistry (see, for example Chem.Ber. 101, 41–50 (1968) and J.Org.Chem. 4248–50 (1978)).

The formula (III) provides a general definition of the organo-magnesium compounds also to be used as starting materials for the reaction according to the invention. In this formula, $R^2$ preferably represents those radicals which have already been mentioned as preferred for this substituent in connection with the description of the substances of the formula (I). Hal preferably represents chlorine or bromine.

The organo-magnesium compounds of the formula (III) are generally known compounds of organic chemistry.

Preferred solvents for the reaction according to the invention are inert organic solvents, in pure form or as mixtures. These solvents include, as preferences, ethers, such as diethyl ether, methyl ethyl ether, tetrahydrofuran or dioxane; aliphatic and aromatic hydrocarbons, such as benzene, toluene or xylene; and hexamethylphosphoric acid triamide.

The reaction temperatures can be varied within a substantial range in carrying out the process according to the invention. In general, the reaction is carried out at between $-50°$ and $+150°$ C., preferably between $-20°$ and $+120°$ C.

The reaction according to the invention can be carried out in the presence of an inert gas, for example nitrogen or helium.

In carrying out the process according to the invention, 1 to 1.5 moles of organo-magnesium compound of the formula (III) are preferably employed per mole of keto-enamine of the formula (II). The compounds of the formula (I) are isolated in the customary manner.

The reduction according to the invention may be carried out in the customary manner, for example by reaction with a complex hydride, if appropriate in the presence of a diluent, or by reaction with aluminum isopropylate in the presence of a diluent.

If a complex hydride is used, possible diluents for the reaction according to the invention are polar organic solvents. These include, as preferences, alcohols, such as methanol, ethanol, butanol and isopropanol, and ethers, such as diethyl ether or tetrahydrofuran. The reaction is in general carried out at from 0° to 30° C., preferably at from 0° to 20° C. For this reduction, about 1 mole of a complex hydride, such as sodium hydride or lithium alanate, is employed per mole of the ketone of the formula (I). In order to isolate the reduced compounds of the formula (I), the residue is taken up in dilute hydrochloric acid and the mixture is then rendered alkaline and extracted with an organic solvent.

Further working up is effected in the customary manner.

If aluminum isopropylate is used, preferred diluents for the reaction according to the invention are alcohols, such as isopropanol, or inert hydrocarbons, such as benzene. The reaction temperatures can again be varied within a substantial range; in general, the reaction is carried out at between 20° and 120° C., preferably at from 50° to 100° C. For carrying out the reaction about 1 to 2 moles of aluminum isopropylate are generally employed per mole of the appropriate ketone of the formula (I). In order to isolate the reduced compounds of the formula (I), the excess solvent is removed by distillation in vacuo and the aluminum compound formed is decomposed with dilute sulphuric acid or sodium hydroxide solution. Further working up is effected in the customary manner.

The following acids can preferably be used for the preparation of physiologically acceptable acid addition salts of the compounds of the formula (I): hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Preferred anions of the salts are those which are derived from the following acids: hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be purified in a known manner, for example by filtration, isolation and, if appropriate, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be employed with particularly good success for combating cereal diseases, such as powdery mildew of barley or cereal (*Erysiphe graminis*) and stripe disease of bareley, Venturia species, such as the apple scab causative organism (*Fusicladium dendriticum*), and Erysiohe species, such as the powdery mildew of cucumber causative organism (*Erysiphe cichoracearum*); and for combating brown rot of tomato (*Phytophthora infestans*). It should be particularly emphasised that the active compounds according to the invention have not only a protective action but in some cases also a systemic action. Thus, it is possible to protect plants from fungal attack if the active compound is fed to the above-ground parts of the plants via the soil and the root or via the seed.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are generally employed per kilogram of seed.

For treatment of soil, active compound concentrations of in general 0.00001 to 0.1% by weight, preferably 0.0001 to 0.02%, are required at the place of action.

When applied in appropriate amounts, the substances according to the invention also exhibit a plant growth-regulating or herbicidal action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

(a) 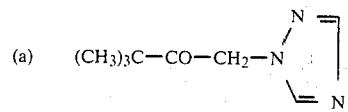

138 g (2 moles) of 1,2,4-triazole were added in portions to 276.4 g (2 moles) of ground potassium carbonate and 259.2 g (2 mol) of α-chloropinacolin in 500 ml of acetone at room temperature, during which the internal temperature rose to the boiling point. The mixture was stirred under reflux for 5 hours and then cooled to room temperature. It was filtered and the filtrate was concentrated by distilling off the solvent in vacuo. The oily residue crystallized after adding benzene. 240.8 g (72% of theory) of 3,3-dimethyl-1-(1,2,4-triazol-1-yl)-butan-2-one of melting point 62°–64° C. were obtained.

(b) 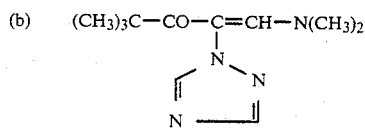

250.8 G (1.5 mole) of 3,3-dimethyl-1-(1,2,4-triazol-1-yl)-butan-2-one and 196 g (1.65 mole) of dimethylformamide dimethyl acetal were heated under reflux for 5 hours. The excess acetal was then distilled off. 306 g (92% of theory) of 4,4-dimethyl-1-dimethylamino-2-(1,2,4-triazol-1-yl)-pent-1-en-3-one with a refractive index $n_D^{20}$ of 1.5310 were obtained.

(c) 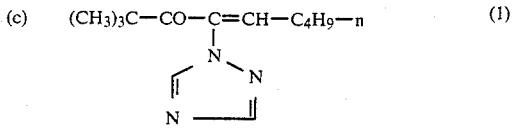 (1)

8.76 g (0.055 mole) of n-butyl-magnesium bromide in 20 ml of ether were added to 11.1 g (0.05 mole) of 4,4-dimethyl-1-dimethylamino-2-(1,2,4-triazol-1-yl)-pent-1-en-3-one in 250 ml of ether under an inert gas at −20° C. in the course of 30 minutes. When the addition had ended, the reaction mixture was allowed to warm to room temperature in the course of about 2 hours. Thereafter, dilute hydrochloric acid was added and the organic phase was separated off, washed with water, dried over sodium sulphate and concentrated. 11.2 g (95% of theory) of 2,2-dimethyl-4-(1,2,4-triazol-1-yl)-4-nonen-3-one with a refractive index $n_D^{20}$ of 1.4858 were obtained.

Example 2

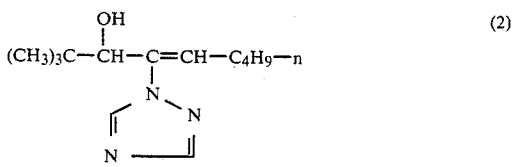 (2)

(Reduction)

1.7 g (0.045 mole) of sodium borohydride, dissolved in 15 ml of water, were added dropwise to 38.5 g (0.17 mole) of 2,2-dimethyl-4-(1,2,4-triazol-1-yl)-5-nonen-3-one (see Example 1) in 160 ml of methanol at 0° C. When the addition had ended, the reaction mixture was allowed to warm to room temperature in the course of 2 hours. Thereafter, a pH value of 6–7 was established with dilute hydrochloric acid and the organic phase was separated off, washed with water, dried over sodium sulphate and concentrated. The residue was taken up in chloroform and the mixture was concentrated again. 34.6 g (89% of theory) of 2,2-dimethyl-4-(1,2,4-triazol-1-yl)-4-nonen-3-ol with a refractive index $n_D^{20}$ of 1.4906 were obtained.

The following compounds of the general formula

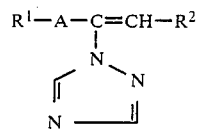

were obtained analogously:

TABLE 2

| Compound No. | $R^1$ | $R^2$ | A | Melting point (°C.) or Refractive index ($n_D^{20}$) |
|---|---|---|---|---|
| 3 | $(CH_3)_3C-$ | $-CH_2-\phi$ | CO | 1.5353 |
| 4 | $(CH_3)_3C-$ | $-C\equiv C-\phi$ | CO | 1.6019 |
| 5 | $(CH_3)_3C-$ | $-C_6H_{13}-n$ | CO | 1.4935 |
| 6 | $(CH_3)_3C-$ | $-C_9H_{19}-n$ | CO | 1.4768 |
| 7 | $(CH_3)_3C-$ | $-C_{10}H_{21}-n$ | CO | 1.4788 |
| 8 | $(CH_3)_3C-$ | $-C_{12}H_{25}-n$ | CO | 1.4865 |
| 9 | $ClCH_2\!-\!C(CH_3)_2-$ | $-C_6H_{13}-n$ | CO | 1.4964 |
| 10 | $(CH_3)_3C-$ | $-CH_3$ | CO | 1.5025 |
| 11 | $(CH_3)_3C-$ | $-C_2H_5$ | CO | 1.4915 |
| 12 | $(CH_3)_3C-$ | $-C(CH_3)_3$ | CO | Viscous oil |
| 13 | $(CH_3)_3C-$ | $-C_7H_{15}-n$ | CO | 1.4708 |
| 14 | $ClCH_2\!-\!C(CH_3)_2-$ | $-C_8H_{17}-n$ | CO | 1.4875 |
| 15 | $ClCH_2\!-\!C(CH_3)_2-$ | $-C_4H_9-n$ | CO | 1.5022 |
| 16 | $(CH_3)_3C-$ | (methyl-indenyl) | CO | 110–13 |
| 17 | $(CH_3)_3C-$ | (methyl-fluorenyl) | CO | 176–78 |
| 18 | $(CH_3)_3C-$ | $-CH(CN)-\phi-Cl$ | CO | 126–27 |
| 19 | $ClCH_2\!-\!C(CH_3)_2-$ | $-C_7H_{15}-n$ | CO | 1.4950 |
| 20 | $FCH_2-C(CH_3)_2-$ | $-CH_3$ | CO | 1.5580 |
| 21 | $FCH_2-C(CH_3)_2-$ | $-C_7H_{15}-n$ | CO | 1.4764 |
| 22 | $Cl-CH_2\!-\!C(CH_3)_2-$ | $-C_2H_5$ | CO | Viscous oil |
| 23 | $(CH_3)_3C-$ | (methyl-indenyl) | CH(OH) | 74–80 |
| 24 | $(CH_3)_3C-$ | $-CH_3$ | CH(OH) | 1.4975 |
| 25 | $(CH_3)_3C-$ | $-C_7H_{15}-n$ | CH(OH) | 1.4767 |
| 26 | $(CH_3)_3C-$ | $-C(CH_3)_3$ | CH(OH) | 35–37 |

TABLE 2-continued

| Compound No. | R[1] | R[2] | A | Melting point (°C.) or Refractive index ($n_D^{20}$) |
|---|---|---|---|---|
| 27 | $(CH_3)_3C-$ | $-CH_2-\phi$ | CH(OH) | 107–09 |
| 28 | $(CH_3)_3C-$ | $-C\equiv C-\phi$ | CH(OH) | 88–91 |
| 29 | $(CH_3)_3C-$ | (fluorenyl) | CH(OH) | 210–14 |
| 30 | $(CH_3)_3C-$ | $-C_8H_{17}-n$ | CH(OH) | 1.4809 |
| 31 | $FCH_2-C(CH_3)_2-$ | $-C_7H_{15}-n$ | CH(OH) | 1.4786 |
| 32 | $(CH_3)_3C-$ | $-CH_3$ | CO | 82 (× $CuCl_2$) |
| 33 | $(CH_3)_3C-$ | $-C_7H_{15}-n$ | CO | Viscous oil (× $CuCl_2$) |
| 34 | $(CH_3)_3C-$ | $-C(CH_3)_3$ | CO | 73–77 (× $CuCl_2$) |
| 35 | $(CH_3)_3C-$ | (fluorenyl) | CO | 148–50 (× $CuCl_2$) |
| 36 | $(CH_3)_3C-$ | (indenyl) | CO | 116–18 (× $CuCl_2$) |
| 37 | $FCH_2-C(CH_3)_2-$ | $-C_9H_{19}-n$ | CO | 1.4679 |
| 38 | $(CH_3)_3C-$ | $C_{18}H_{37}-n$ | CO | 1.4696 |
| 39 | $(CH_3)_3C-$ | $-C\equiv C-\phi$ | CO | 75–80 (× $CuCl_2$) |
| 40 | $(CH_3)_3C-$ | $-C_2H_5$ | CO | 70 (× $CuCl_2$) |
| 41 | $(CH_3)_3C-$ | $-C_{12}H_{25}-n$ | CH(OH) | 20 |
| 42 | $(CH_3)_3C-$ | $-CH_2-CH(CH_3)_2$ | CO | 1.4861 |
| 43 | $(CH_3)_3C-$ | $-CH_2CH_2CH(CH_3)_2$ | CO | 1.4834 |
| 44 | $(CH_3)_3C-$ | $-CH_2-CH(CH_3)_2$ | CH(OH) | 1.4870 |
| 45 | $(CH_3)_3C-$ | $-CH_2CH_2CH(CH_3)_2$ | CH(OH) | 1.4850 |

The activity of the compounds of this invention is illustrated by the following biological examples wherein the compounds according to the present invention are each identified by the number (given in brackets) from the preparative examples and Table 2 hereinabove.

The known comparison compounds are identified as follows:

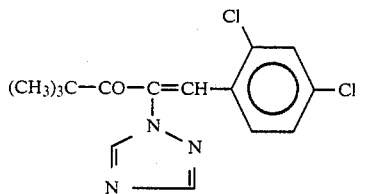

(A)

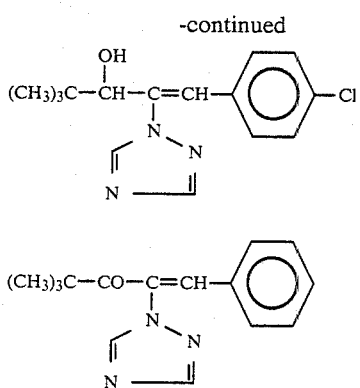

(B)

(C)

Example 3

Erysiphe test (barley)/protective/

Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis* f.sp. *hordei*.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a significantly superior activity compared with the prior art was shown, for example, by the compounds (3), (13), (16), (4), (34), (2), (24), (27), and (26), as can be seen from the following test results:

TABLE 3

Erysiphe test (barley)/protective

| Active compound | Active compound concentration in the spray liquor in % by weight | Disease infestation in % of the untreated control |
|---|---|---|
| (A) | 0.025 | 100 |
| (3) | 0.025 | 0.0 |
| (13) | 0.02 | 25.0 |
| (16) | 0.025 | 21.3 |
| (4) | 0.025 | 0.0 |
| (34) | 0.025 | 31.3 |
| (2) | 0.025 | 0.0 |
| (24) | 0.025 | 33.8 |
| (27) | 0.025 | 0.0 |
| (26) | 0.025 | 21.3 |

Example 4

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Drechslera graminea* (commonly described as *Helminthosporium gramineum*), was shaken with the dressing in a closed glass flask. The seed, on moist filter paper discs in closed Petri dishes, was exposed to a temperature of 4° C. for 10 days in a refrigerator. The germination of the barley, and possibly also of the fungus spores, was thereby initiated. 2 batches of 50 grains of the pregerminated barley were subsequently sown 3 cm deep in Frühstorfer standard soil and cultivated in a greenhouse at temperatures of about 18° C. in seed boxes which were exposed to light for 16 hours daily. The typical sysmptoms of the stripe disease developed within 3 to 4 weeks.

After this time, the number of diseased plants was determined as a percentage of the total number of emerged plants. The fewer plants were diseased, the more effective was the active compound.

In this test, for example, compound (2) exhibited a very good action which was superior to that of compound (B) known from the prior art, as can be seen from the following test results:

TABLE 4

Seed dressing test/strip disease of barley

| Active compound | Active compound concentration in the dressing in % | Amount of dressing applied in g/kg of seed | Number of plants affected by stripe disease in % of the total number of emerged plants |
|---|---|---|---|
| undressed | — | — | 42.1 |
| (B) | 10 | 2 | 45.3 |
| (2) | 10 | 2 | 2.1 |

Example 5

Fusicladium test (apple)/protective

Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contains the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18° to 20° C. and at a relative atmospheric humidity of 100%.

The plants were then again brought into a greenhouse for 14 days.

15 days after inoculation, the infection of the seedlings was determined. The assessment data were converted to percent infection. 0% denoted no infection and 100% denoted that the plants were totally infected.

In this test, for example, compounds (27), (26), (36), (34), (33), (32), (13) and (12) exhibited a very good action which was superior to that of compound (C) known from the prior art, as can be seen from the following test results.

TABLE 5

Fusicladium test (apple)/protective

| Active compound | Infection in % at an active compound concentration of 0.01% |
|---|---|
| (C) | 77 |
| (27) | 10 |
| (26) | 21 |
| (36) | 20 |
| (34) | 11 |
| (33) | 2 |
| (32) | 12 |
| (13) | 20 |
| (12) | 35 |

It will be understood that the specification and examples are illustrative but not limitative of the present invention and that other embodiments within the spirit and scope of the invention will suggest themselves to those skilled in the art.

We claim:

1. A triazolyl-vinyl ketone or carbinol of the formula

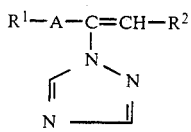

in which

A represents the keto group or a CH(OH) grouping, $R^1$ is tert.-butyl, chloro-tert.-butyl, fluoro-tert.-butyl, dichloro-tert.-butyl or difluoro-tert.-butyl, and $R^2$ is n-butyl or n-heptyl, is benzyl, optionally substituted on the phenyl with halogen, alkyl with 1 to 4 carbon atoms, alkoxy or alkylthio with 1 to 4 carbon atoms or halogenoalkoxy or halogenoalkylthio with 1 to 4 carbon atoms and 1 to 5 halogen atoms, or is phenylethynyl, or an addition product thereof with a physiologically acceptable acid or a metal salt.

2. A compound according to claim 1, wherein said compound is 2,2-dimethyl-4-(1,2,4-triazol-1-yl)-4-nonen-3-ol of the formula

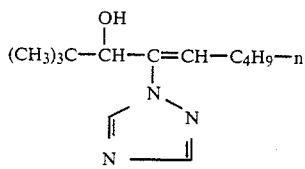

or an addition product thereof with a physiologically acceptable acid or metal salt.

3. A compound according to claim 1, wherein said compound is 2,2-dimethyl-4-(1,2,4-triazol-1-yl)-6-phenyl-4-hexen-3-one of the formula

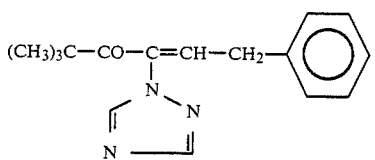

or an addition product thereof with a physiologically acceptable acid or metal salt.

4. A compound according to claim 1, wherein said compound is 2,2-dimethyl-4-(1,2,4-triazol-1-yl)-4-hepten-6-yn-3-one of the formula

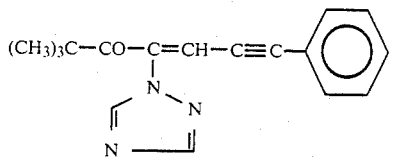

or an addition product thereof with a physiologically acceptable acid or metal salt.

5. A compound according to claim 1, wherein said compound is 2,2-dimethyl-4-(1,2,4-triazol-1-yl)-4-hexen-3-ol of the formula

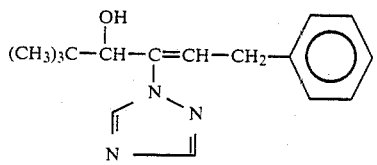

or an addition product thereof with a physiologically acceptable acid or metal salt.

6. A compound according to claim 1, wherein said compound is 2,2-dimethyl-4-(1,2,4-triazol-1-yl)-4-dodecen-3-one of the formula

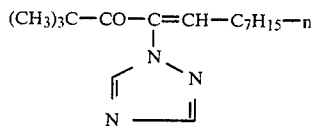

or an addition product thereof with a physiologically acceptable acid or metal salt.

7. A fungicidal composition comprising a fungicidally effective amount of a compound according to claim 1 in admixture with a diluent.

8. A method of combating fungi comprising applying to the fungi, or to a habitat thereof, a fungicidally effective amount of a compound according to claim 1.

9. The method according to claim 8, wherein such compound is 2,2-dimethyl-4-(1,2,4-triazol-1-yl)-4-nonen-3-ol,
2,2-dimethyl-4-(1,2,4-triazol-1-yl)-6-phenyl-4-hexen-3-one,
2,2-dimethyl-4-(1,2,4-triazol-1-yl)-4-hepten-6-yn-3-one,
2,2-dimethyl-4-(1,2,4-triazol-1-yl)-4-hexen-3-ol or
2,2-dimethyl-4-(1,2,4-triazol-1-yl)-4-dodecen-3-one, or an addition product thereof with a physiologically acceptable acid or a metal salt.

* * * * *